United States Patent [19]

Rogers et al.

[11] Patent Number: 4,685,959

[45] Date of Patent: Aug. 11, 1987

[54] PYRIDYLOXYPHENOXYALKANOATES, ALKENOATES AND DERIVATIVES THEREOF, USEFUL AS HERBICIDAL AGENTS

[75] Inventors: Richard B. Rogers; Cleve A. I. Goring, both of Midland, Mich.

[73] Assignee: The Dow Chemical Company, Midland, Mich.

[21] Appl. No.: 809,829

[22] Filed: Dec. 17, 1985

[51] Int. Cl.$^4$ .................. A01N 43/40; C07D 211/72; C07D 211/76

[52] U.S. Cl. ........................................ 71/94; 546/291; 546/293; 546/300; 546/302

[58] Field of Search .............. 546/291, 293, 300, 302; 71/94

[56] References Cited

U.S. PATENT DOCUMENTS

| | | | |
|---|---|---|---|
| 4,429,167 | 1/1984 | Lee | 546/291 |
| 4,448,965 | 5/1984 | Henrick | 546/302 |
| 4,448,966 | 5/1984 | Lee | 546/302 |
| 4,467,092 | 8/1984 | Kohn et al. | 546/291 |
| 4,469,872 | 9/1984 | Anderson et al. | 546/302 |
| 4,477,672 | 10/1984 | Kohn et al. | 546/294 |
| 4,483,992 | 11/1984 | Kohn et al. | 546/302 |
| 4,499,271 | 2/1985 | Kohn et al. | 546/22 |
| 4,505,743 | 3/1985 | Schurter et al. | 71/94 |
| 4,508,906 | 4/1985 | Bamberg et al. | 546/300 |
| 4,520,199 | 5/1985 | Kohn et al. | 546/302 |
| 4,522,647 | 6/1985 | Anderson et al. | 71/94 |
| 4,529,438 | 7/1985 | Lee | 71/94 |
| 4,561,882 | 12/1985 | Lee | 71/94 |

*Primary Examiner*—Henry R. Jiles
*Assistant Examiner*—J. Richter
*Attorney, Agent, or Firm*—Joseph T. Majka; Ronald G. Brookens

[57] ABSTRACT

Novel pyridyloxyphenoxyalkanoates, alkenoates, R-enantiomers and derivatives thereof possess herbicidal activity selectively in the presence of broadleaf crops with preemergent or postemergent applications.

87 Claims, No Drawings

PYRIDYLOXYPHENOXYALKANOATES, ALKENOATES AND DERIVATIVES THEREOF, USEFUL AS HERBICIDAL AGENTS

BACKGROUND OF THE INVENTION

The present invention relates to certain novel pyridyloxyphenoxyalkanoates and alkenoates, and to the R-enantiomers thereof which are useful as herbicides. The present invention also relates to herbicidal compositions containing these novel compounds; to methods of using these compounds for the control of weeds in non-crop areas as well as in the presence of valuable crops; and to novel intermediates used to make these compounds.

U.S. Pat. No. 4,505,743 describes novel α-[4-(3'-fluoro-5'-halopyridyl-2'-oxy)-phenoxy]propionic acid derivatives having herbicidal activity.

SUMMARY OF THE INVENTION

The present invention is directed to certain pyridyloxyphenoxyalkanoates and alkenoates and their R-enantiomers thereof, of the following formula:

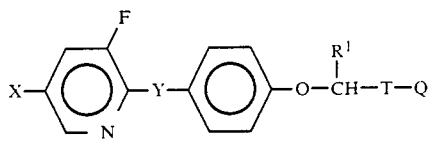
(A)

wherein
X represents $-Cl$, $-Br$, $-F$, $-I$, $-CF_3$, $-CHF_2$ or $-CClF_2$;
Y represents oxygen or sulfur;
T represents

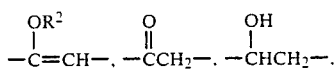

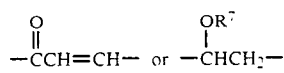

$R^1$ is hydrogen or loweralkyl;
$R^2$ is loweralkyl;
$R^7$ is loweralkyl, acyl or sulfonyl;
Q is

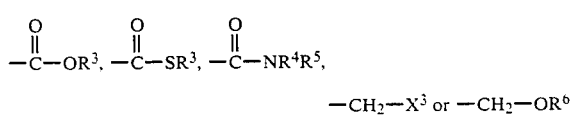

in which
$R^3$ is hydrogen, loweralkyl, lowerhaloalkyl, lowercyanoalkyl, loweralkenyl, lowerhaloalkenyl, loweralkynyl, loweralkoxyalkyl, lowerdialkylaminoalkyl, loweralkylthioalkyl, loweralkylsulfinylalkyl, loweralkylsulfonylalkyl, tetrahydrofuranylmethyl, tetrahydropyranylmethyl, benzyl, halobenzyl, loweralkylbenzyl, loweralkoxybenzyl, phenyl, halophenyl, loweralkoxyphenyl, loweralkylphenyl, cycloalkyl, cycloalkalkyl, N-alkylideneamino, sodium, potassium, magnesium or calcium; and
Q is H when T is

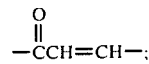

each of $R^4$ and $R^5$ independently selected from hydrogen, loweralkyl, lowerhydroxyalkyl, loweralkoxyalkyl, loweralkylsulfonyl, loweralkenyl, loweralkynyl, lowerhaloalkenyl, cycloalkyl, phenyl, halophenyl, loweralkoxyphenyl, loweralkylphenyl, cyano, amino, lower dialkylamino, lower monoalkylamino or loweralkoxy;
$X^3$ is bromo, chloro, fluoro or iodo; and
$R^6$ is hydrogen or acyl.

In the description and claims hereinafter, each of T, Y, $R^1$, $R^2$, $R^3$, $R^4$, $R^5$, $R^6$, $R^7$, Q, X, and $X^3$ is as defined above, unless otherwise specified.

The term "loweralkyl" refers to a straight or branched alkyl group of one to six carbon atoms.

The term "loweralkoxy" refers to an alkoxy group of one to six carbon atoms.

The term "loweralkoxycarbonyl" refers to an alkoxycarbonyl group of two to seven carbon atoms branched or unbranched, including the carbonyl carbon.

The term "acyl" refers to a carbonyl group such as a lower aliphatic acyl group of one to six carbon atoms, an aryl acyl group of six to twelve carbon atoms, an alkoxycarbonyl group

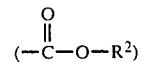

of one to six carbon atoms or to an aryloxycarbonyl group of six to twelve carbon atoms. Typical acyl groups include acetyl, benzoyl, p-chlorobenzoyl, ethoxycarbonyl and the like.

The term "sulfonyl" ($-SO_2R$) refers to a sulfonic acid derivative such as a lower aliphatic sulfonyl group of one to six carbon atoms or aryl sulfonyl group of six to twelve carbon atoms.

The term "loweralkenyl" refers to an alkenyl group of two to six carbon atoms with one double bond such as allyl and n-buten-2-yl.

The term "loweralkynyl" refers to an alkynyl group of two to six carbon atoms with one triple bond such as propargyl.

The term "cycloalkyl" refers to a cycloalkyl group of three to six carbon atoms.

The term "cycloalkalkyl" refers to a cycloalkalkyl group of four to seven carbon atoms.

The term "halo" refers to a bromo, chloro, fluoro, or iodo group.

The compounds of the above Formula (A) hereinafter referred to as "active ingredients", are active as herbicides in the presence of broadleaf crops and in certain cases are substantially non-phytotoxic to small grain crops such as wheat and barley. The compounds have low mammalian toxicity. Accordingly, the present invention also encompasses herbicidal compositions containing one or more active ingredients as well as methods of controlling unwanted vegetation. Such methods comprise, for example, applying a herbicidally effective amount of one or more active ingredients preemergently or postemergently to the locus of the undesired vegetation, and particularly to the locus where a valuable crop is to germinate and grow.

The preparation of fluoropyridyloxypheoxy propionates and derivatives thereof have been described in U.S. Pat. No. 4,505,743 whose preparative teachings are incorporated herein by reference.

A variety of herbicidal compounds containing substituted pyridyl and phenoxy moieties joined via a bivalent —O— and —S— are described in the art. For example U.S. Pat. Nos. 4,046,553; 4,317,913; 4,267,336; 4,213,774; 4,324,627 and 4,309,547 and U.S. patent application Ser. Nos. 262,063 and 261,109, both filed July 30, 1980; Ser. No. 817,943, filed July 22, 1977 and Ser. No. 918,550, filed June 23, 1978, all describe such compounds, methods of making them, compositions containing them and methods of utilizing said compositions. These teachings are incorporated herein by reference.

Preparation of various pentanoate alcohols, esters, ethers and ketones of substituted phenoxyphenoxy or pyridyloxyphenoxy compounds can be found in U.S. Pat. Nos. 4,408,076; 4,429,167; 4,469,872; 4,520,199 and 4,529,438, whose preparative teachings are all incorporated herein by reference.

Particular embodiments of Formula A are illustrated in the following formulas (B), (C), (D), (E) and (F):

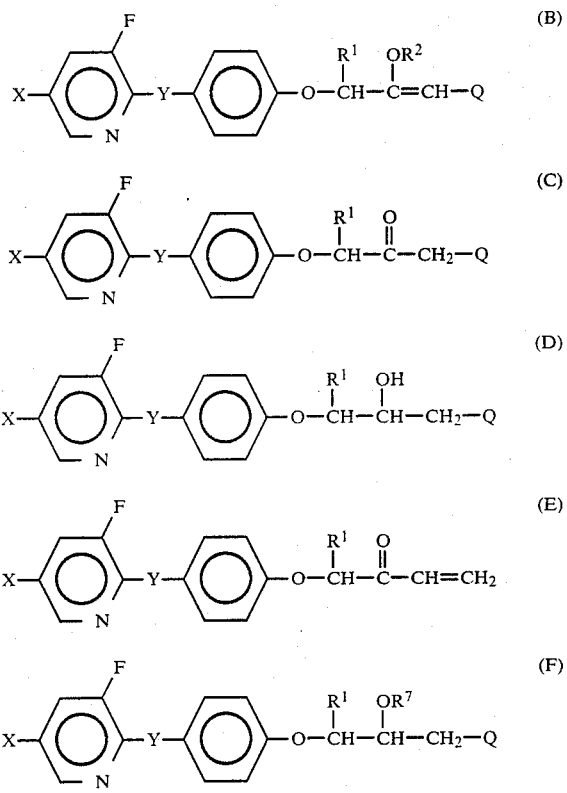

wherein X, $R^1$, $R^2$, $R^7$ and Q are as defined hereinbefore.

The compounds of formula (B) wherein Q is

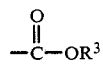

can be produced by the reaction of a phenol of Formula (I)

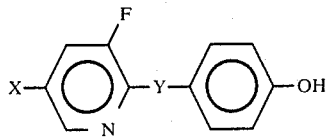

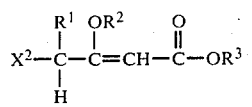

with a 4-halo compound of Formula (II) wherein $X^2$ represents bromo, chloro or iodo in the presence of a base such as alkali metal hydroxide or alkali metal carbonate. The reaction is generally conducted at about room temperature to reflux temperature in an organic solvent such as dimethylformamide (DMF), acetone, tetrahydrofuran (THF), dimethylacetamide (DMA), dimethylsulfoxide (DMSO), or the like using about equimolar amounts of base, a phenol of Formula (I) and a 4-halo compound of Formula (II).

The thio compounds of Formula (B) wherein Q is —COSR$^3$ can be prepared starting with a carboxylic acid of Formula (B) which is converted into the acid halide and then reacted with a mercaptan. Alternatively, a phenol of Formula (I) is reacted with a 4-halo thioester of the general Formula (II) above in the presence of base.

An amide of Formula (B) can be prepared by the reaction of an acid halide of an acid of Formula (B) with the appropriate amine.

An alcohol of Formula (B) wherein Q is —CH$_2$—OH can be prepared by reduction of an acid or ester of Formula (B) using, for example, lithium borohydride or lithium aluminumhydride in ether or THF at a low temperature. Esters of an alcohol of Formula (B) wherein Q is CH$_2$OR$_6$ and R$_6$ is acyl can be prepared by the reaction of an acyl halide or acyl anhydride in pyridine with an alcohol of Formula B wherein Q is CH$_2$OH at about room temperature or lower.

A halide of the present invention of Formula (B) wherein Q is —CH$_2$—X$^3$ can be prepared by reaction of an alcohol of Formula (B) wherein Q is —CH$_2$—OH with phosphorus tribromide, phosphorus trichloride, or triphenylphosphine dihalide in acetonitrile.

In another embodiment of the present invention, there is provided 3-oxo derivatives of Formula (C) which can be derived from the novel compounds of Formula (B). The compounds of Formula (C) are useful for the control of weeds.

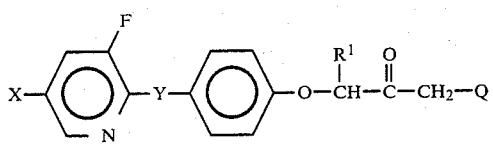

A compound of Formula (C) can be prepared by the reaction of a 3-alkoxy compound of Formula (B) such as a 3-methoxy compound of Formula (B) with an acid such as dilute perchloric acid or acetic acid in an organic solvent such as methylenedichloride, carbon tetrachloride or THF. The reaction is usually conducted at about room temperature or lower.

In another embodiment of the present invention, there is provided compounds of Formula (D), which can be prepared by selective reduction of a compound of Formula (C) using sodium borohydride in alcohol at low temperature.

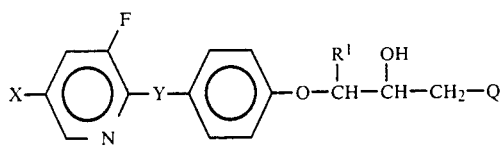
(D)

The alcohols of Formula (D) and carboxylic esters thereof are useful for the control of weeds.

In another embodiment of the present invention, there is provided compounds of Formula (E) which are useful for the control weeds.

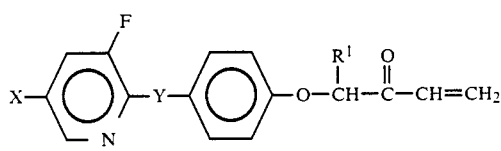
(E)

The compounds of Formula (E) can be prepared by treating an alcohol of Formula (B) wherein Q is —CH$_2$—OH with perchloric acid.

Carboxylic esters of Formula (C) wherein Q is

can be prepared by the following outlined method also:

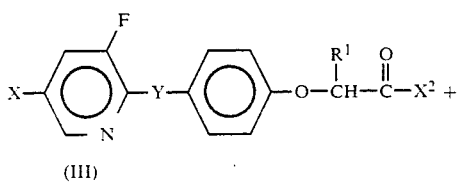
(III)

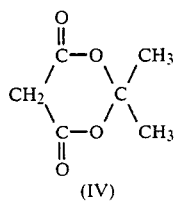
(IV)

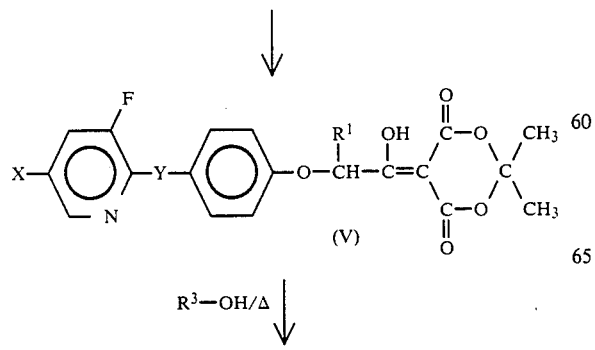
(V)

R$^3$—OH/Δ

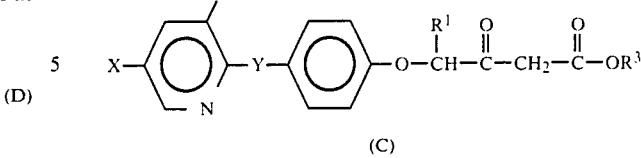
(C)

The compounds of Formula (F) wherein R$^7$ is loweralkyl can be synthesized by the reaction of an alcohol of Formula (D) with a diazoalkyl in an organic solvent inert to the reaction, such as ether, and catalyzed by silica gel, following the procedure described by K. Ohno et al., Tetrahedron Letters No. 45, p. 4405 (1979).

The compounds of Formula (F) wherein R$^7$ is acyl or sulfonyl can be prepared by reacting an alcohol of Formula (D) with an acyl or sulfonyl halide, or an acyl anhydride in an inert solvent in the presence of a tertiary amine base at low temperature:

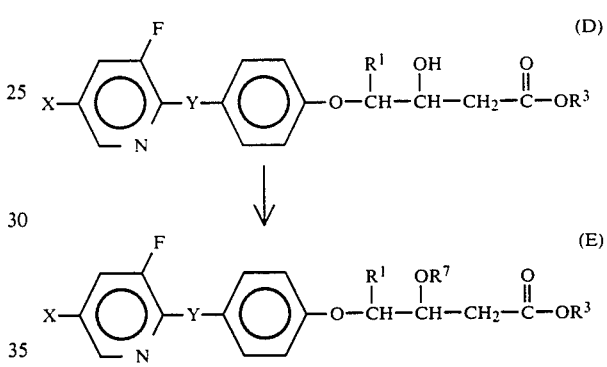
(D)

↓

(E)

PREPARATION OF STARTING MATERIALS

The preparative teachings of these above cited patents are incorporated herein by reference.

DETAILED DESCRIPTION OF THE INVENTION

The following terms have the meaning indicated as used herein and the appended claims.

The term "herbicide" is used herein to mean an active ingredient which controls or adversely modifies the growth of plants. By "growth controlling" or "herbicidally-effective" amount is meant an amount of active ingredient which causes an adversely modifying effect and includes deviations from natural development, killing, regulation, dessication, retardation, and the like.

The term "plants", when used herein, is meant to include germinant seeds, emerging seedlings, rhizomes, stolons and other underground propagules, as well as established vegetation.

The compounds of the present invention contain the asymmetric center

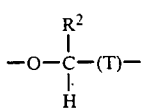

and thus can exist in optically active stereoisomeric forms such as the R and S enantiomeric forms. In situations where T is

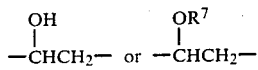

the compound may contain a second R isomer. The various mixtures and racemates of the above isomers are within the scope of the present invention. Additionally, the R enantiomer of such compounds are more active biologically than the S enantiomer and may be prepared and used whenever the greater activity justifies the extra expenses of preparing the more active isomer.

A general discussion of the isomer activity difference phenomenon can be found in A. Albert, Selective Toxicity, 4th ed., Met Luen & Co., Ltd., London, 1968, pp. 387–390 and more particular discussions in A. Fredga and B. Åberg, "Stereoisomerism in plant growth regulators of the auxin type", Ann. Rev. Plant Physiology 16:53–72, 1965 and in E. J. Lien, J. F. R. DeMiranda and E. J. Airens, "Quantitative structure-activity correlation of optical isomers", Molecular Pharmacology 12:598–604, 1976.

The compounds of the present invention, i.e., active ingredients, in the form of racemic mixtures or in mixtures containing varying amounts of their resolved isomers, preferably containing greater than 50 percent of the R-enantiomer, are suitable for use in methods for the preemergent and postemergent control of grasses, such as, barnyard grass, crabgrass, yellow foxtail and johnson grass, in the presence of broadleaf crops, such as, cotton, soybeans and sugar beets. Further, the compounds of Formula (A) above where X is —Cl, —Br or —I are selective for small grains, such as, wheat and barley.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

The active ingredients of the present invention can also be applied, preferably, with a crop oil or a vegetable oil. Crop oil include, for example, the paraffinic oils pressed or dry-distilled from paraffin distillate. Vegetable oils include, for example, soybean oil, corn oil, sunflower oil and the like.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat ® 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic ® 61 (molecular weight about 1000), polyethylene glycol ester of tall oil acids, sodium octophenoxyethoxyethyl sulfate, tris(polyoxyethylene)sorbitan monostearate (Tween ® 60), and sodium dihexylsulfosuccinate.

The concentration of the active ingredients in solid or liquid compositions generally is from about 0.003 to 95 percent by weight or more. Concentrations from 0.05 to about 50 percent by weight are often employed. In compositions to be employed as concentrates, the active ingredient can be present in a concentration from about 5 to 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, blackgrass, wild oats, barnyard grass and crabgrass in preemergent operations and also against the same grasses in postemergent operations. The active ingredients possess desirable herbicidal activity against the grassy weeds, described above, while at the same time are tolerant or selective to broadleaf crops, such as, cotton, soybeans and sugar beets and in certain cases, small grain cereals, i.e., when X of Formula A is —Cl, —Br or —I.

The exact rate to be applied is dependent not only on a specific active ingredient being applied, but also on a particular action desired (e.g., general or selective control), the plant species to be modified, and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from 0.1 to about 5 pounds/acre, but higher rates may be appropriate in some cases such as 20 pounds/acre or more. In preemergent operations for selective uses a dosage of about 0.01 to about 10 pounds/acre or more is generally applicable, a rate of 0.05 to 4 pounds/acre being preferred and about 0.1 to about 2 pounds/acre being most preferred. For controlling an infestation of annuals, a dosage of about 0.1 to 0.5 pound/acre is generally utilized. When the infestation consists largely of perennials, a dosage of from 0.1 to 4, preferably 0.5 to 2.0 pounds/acre should be employed.

In postemergent operations a dosage of 0.01 to 20 pounds/acre or more is generally applicable, although not all compounds are equally effective and some weeds are more difficult to control. A dosage rate in the range of 0.05 to 0.75 pounds/acre is preferred in selective postemergent control of annual grassy weeds, while about 0.25 to about 5 pounds/acre is preferred and more preferably 0.25 to about 2 pounds/acre for the selective postemergent control of perennial grassy weeds.

In further embodiments, the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

What is claimed is:
1. A compound of the formula

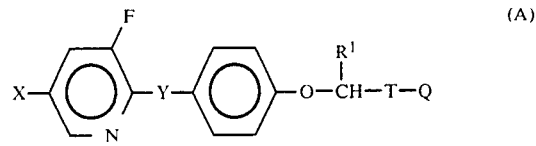

wherein
X represents —Cl, —Br, —F, —I;
Y represents oxygen or sulfur;
T represents

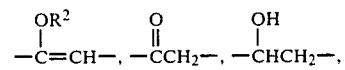

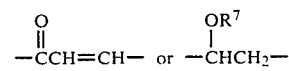

$R^1$ is hydrogen or loweralkyl;
$R^2$ is loweralkyl;
$R^7$ is loweralkyl, acyl or sulfonyl;
Q is

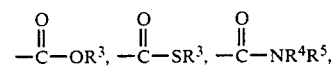

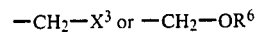

in which
$R^3$ is hydrogen, loweralkyl, lowerhaloalkyl, lowercyanoalkyl, loweralkenyl, lowerhaloalkenyl, loweralkynyl, loweralkoxyalkyl, lowerdialkylaminoalkyl, loweralkylthioalkyl, loweralkylsulfinylalkyl, loweralkylsulfonylalkyl, tetrahydrofuranylmethyl, tetrahydropyranylmethyl, benzyl, halobenzyl, loweralkylbenzyl, loweralkoxybenzyl, phenyl, halophenyl, loweralkoxyphenyl, loweralkylphenyl, cycloalkyl, cycloalkalkyl, N-alkylideneamino, sodium, potassium, magnesium or calcium; and Q is H when T is

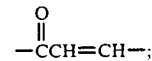

each of $R^4$ and $R^5$ independently selected from hydrogen, loweralkyl, lowerhydroxyalkyl, loweralkoxyalkyl, loweralkylsulfonyl, loweralkenyl, loweralkynyl, lowerhaloalkenyl, cycloalkyl, phenyl, halophenyl, loweralkoxyphenyl, loweralkylphenyl, cyano, amino, lower dialkylamino, lower monoalkylamino or loweralkoxy;
$X^3$ is bromo, chloro, fluoro or iodo; and
$R^6$ is hydrogen or acyl wherein in the above, acyl represents a $C_1$-$C_6$ aliphatic acyl, or $C_1$-$C_6$ alkoxycarbonyl; anylacyl represents benzoyl; and cycloalkyl consists of $C_3$-$C_6$ carbon atoms.
2. The compound of claim 1 which is

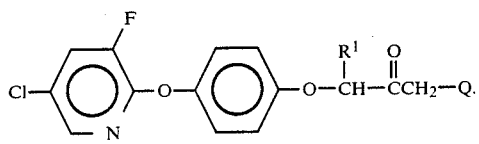

3. The compound of claim 1 which is

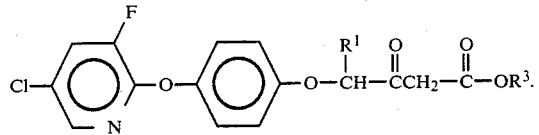

4. The compound of claim 1 which is

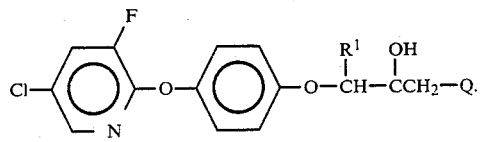

5. The compound of claim 1 which is

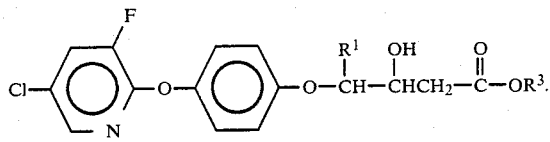

6. The compound of claim 1 which is

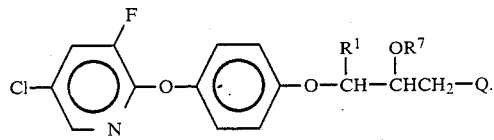

7. The compound of claim 1 which is

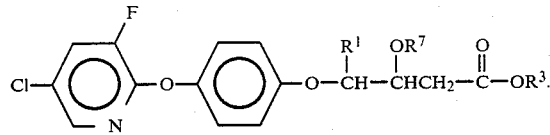

8. The compound of claim 1 which is

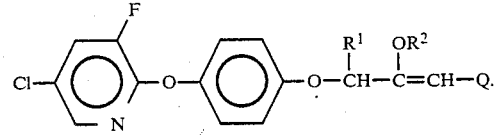

9. The compound of claim 1 which is

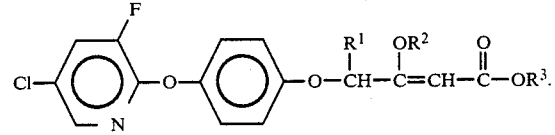

10. The compound of claim 1 which is

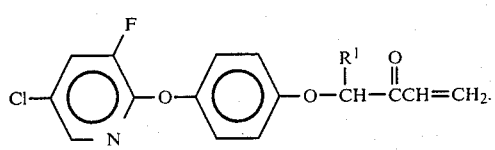

11. The compound of claim 1 which is

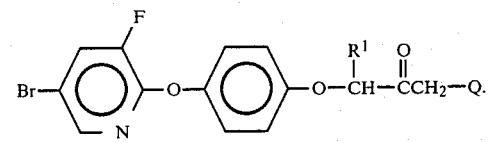

12. The compound of claim 1 which is

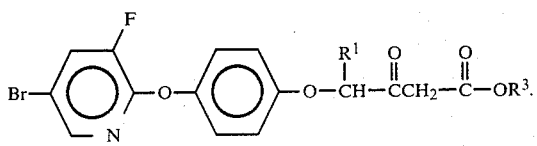

13. The compound of claim 1 which is

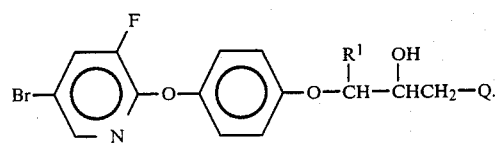

14. The compound of claim 1 which is

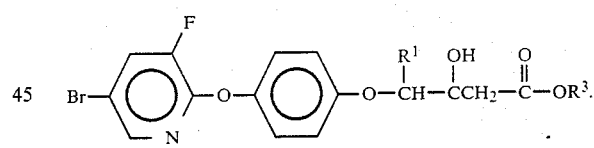

15. The compound of claim 1 which is

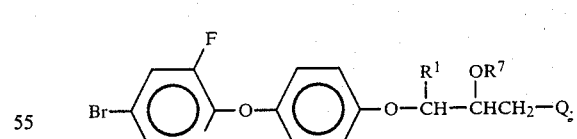

16. The compound of claim 1 which is

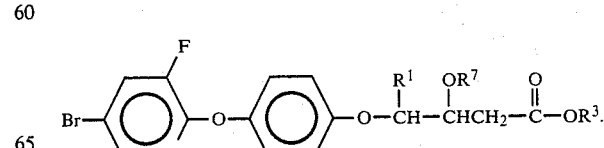

17. The compound of claim 1 which is

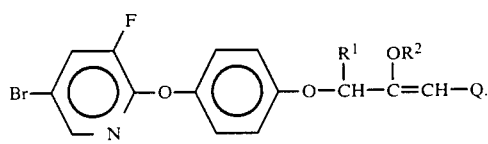

18. The compound of claim 1 which is

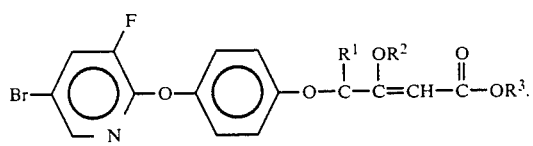

19. The compound of claim 1 which is

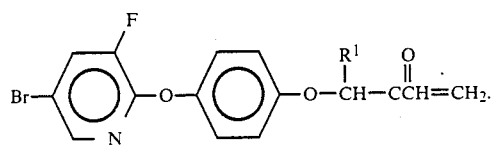

20. The compound of claim 1 which is

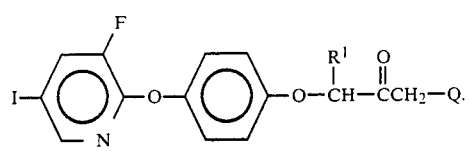

21. The compound of claim 1 which is

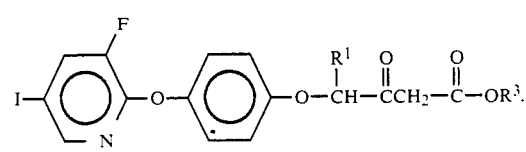

22. The compound of claim 1 which is

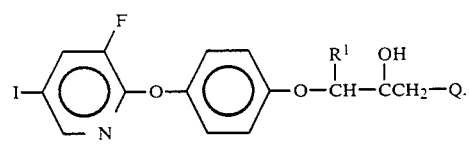

23. The compound of claim 1 which is

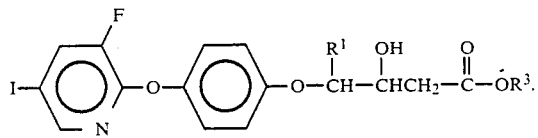

24. The compound of claim 1 which is

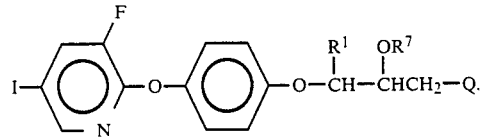

25. The compound of claim 1 which is

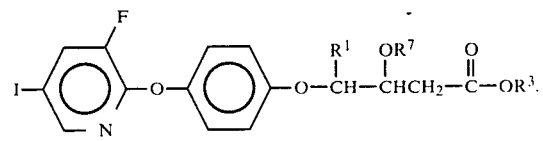

26. The compound of claim 1 which is

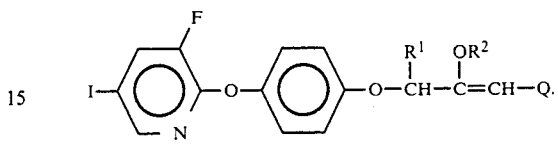

27. The compound of claim 1 which is

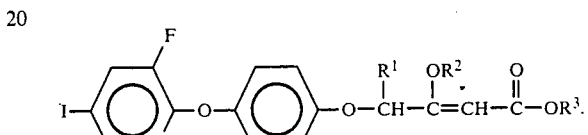

28. The compound of claim 1 which is

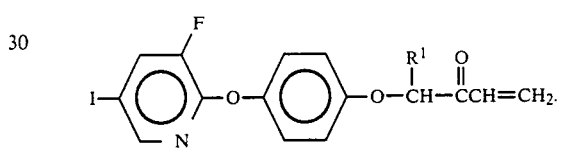

29. The compound of claim 1 which is

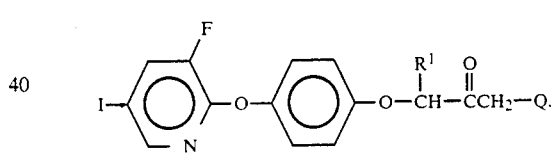

30. A herbicidal composition which comprises a herbicidally-effective amount of a compound of claim 1 in admixture with a suitable carrier material.

31. A herbicidal composition which comprises a herbicidally-effective amount of a compound of claim 2 in admixture with a suitable carrier material.

32. A herbicidal composition which comprises a herbicidally-effective amount of a compound of claim 3 in admixture with a suitable carrier material.

33. A herbicidal composition which comprises a herbicidally-effective amount of a compound of claim 4 in admixture with a suitable carrier material.

34. A herbicidal composition which comprises a herbicidally-effective amount of a compound of claim 5 in admixture with a suitable carrier material.

35. A herbicidal composition which comprises a herbicidally-effective amount of a compound of claim 6 in admixture with a suitable carrier material.

36. A herbicidal composition which comprises a herbicidally-effective amount of a compound of claim 7 in admixture with a suitable carrier material.

37. A herbicidal composition which comprises a herbicidally-effective amount of a compound of claim 8 in admixture with a suitable carrier material.

38. A herbicidal composition which comprises a herbicidally-effective amount of a compound of claim 9 in admixture with a suitable carrier material.

39. A herbicidal composition which comprises a herbicidally-effective amount of a compound of claim 10 in admixture with a suitable carrier material.

40. A herbicidal composition which comprises a herbicidally-effective amount of a compound of claim 11 in admixture with a suitable carrier material.

41. A herbicidal composition which comprises a herbicidally-effective amount of a compound of claim 12 in admixture with a suitable carrier material.

42. A herbicidal composition which comprises a herbicidally-effective amount of a compound of claim 13 in admixture with a suitable carrier material.

43. A herbicidal composition which comprises a herbicidally-effective amount of a compound of claim 14 in admixture with a suitable carrier material.

44. A herbicidal composition which comprises a herbicidally-effective amount of a compound of claim 15 in admixture with a suitable carrier material.

45. A herbicidal composition which comprises a herbicidally-effective amount of a compound of claim 16 in admixture with a suitable carrier material.

46. A herbicidal composition which comprises a herbicidally-effective amount of a compound of claim 17 in admixture with a suitable carrier material.

47. A herbicidal composition which comprises a herbicidally-effective amount of a compound of claim 18 in admixture with a suitable carrier material.

48. A herbicidal composition which comprises a herbicidally-effective amount of a compound of claim 19 in admixture with a suitable carrier material.

49. A herbicidal composition which comprises a herbicidally-effective amount of a compound of claim 20 in admixture with a suitable carrier material.

50. A herbicidal composition which comprises a herbicidally-effective amount of a compound of claim 21 in admixture with a suitable carrier material.

51. A herbicidal composition which comprises a herbicidally-effective amount of a compound of claim 22 in admixture with a suitable carrier material.

52. A herbicidal composition which comprises a herbicidally-effective amount of a compound of claim 23 in admixture with a suitable carrier material.

53. A herbicidal composition which comprises a herbicidally-effective amount of a compound of claim 24 in admixture with a suitable carrier material.

54. A herbicidal composition which comprises a herbicidally-effective amount of a compound of claim 25 in admixture with a suitable carrier material.

55. A herbicidal composition which comprises a herbicidally-effective amount of a compound of claim 26 in admixture with a suitable carrier material.

56. A herbicidal composition which comprises a herbicidally-effective amount of a compound of claim 27 in admixture with a suitable carrier material.

57. A herbicidal composition which comprises a herbicidally-effective amount of a compound of claim 28 in admixture with a suitable carrier material.

58. A herbicidal composition which comprises a herbicidally-effective amount of a compound of claim 29 in admixture with a suitable carrier material.

59. A method for the control of weeds comprising an application of a herbicidally-effective amount of a compound of claim 1 to the locus of said weeds.

60. A method for the control of weeds comprising an application of a herbicidally-effective amount of a compound of claim 2 to the locus of said weeds.

61. A method for the control of weeds comprising an application of a herbicidally-effective amount of a compound of claim 3 to the locus of said weeds.

62. A method for the control of weeds comprising an application of a herbicidally-effective amount of a compound of claim 4 to the locus of said weeds.

63. A method for the control of weeds comprising an application of a herbicidally-effective amount of a compound of claim 5 to the locus of said weeds.

64. A method for the control of weeds comprising an application of a herbicidally-effective amount of a compound of claim 6 to the locus of said weeds.

65. A method for the control of weeds comprising an application of a herbicidally-effective amount of a compound of claim 7 to the locus of said weeds.

66. A method for the control of weeds comprising an application of a herbicidally-effective amount of a compound of claim 8 to the locus of said weeds.

67. A method for the control of weeds comprising an application of a herbicidally-effective amount of a compound of claim 9 to the locus of said weeds.

68. A method for the control of weeds comprising an application of a herbicidally-effective amount of a compound of claim 10 to the locus of said weeds.

69. A method for the control of weeds comprising an application of a herbicidally-effective amount of a compound of claim 11 to the locus of said weeds.

70. A method for the control of weeds comprising an application of a herbicidally-effective amount of a compound of claim 12 to the locus of said weeds.

71. A method for the control of weeds comprising an application of a herbicidally-effective amount of a compound of claim 13 to the locus of said weeds.

72. A method for the control of weeds comprising an application of a herbicidally-effective amount of a compound of claim 14 to the locus of said weeds.

73. A method for the control of weeds comprising an application of a herbicidally-effective amount of a compound of claim 15 to the locus of said weeds.

74. A method for the control of weeds comprising an application of a herbicidally-effective amount of a compound of claim 16 to the locus of said weeds.

75. A method for the control of weeds comprising an application of a herbicidally-effective amount of a compound of claim 17 to the locus of said weeds.

76. A method for the control of weeds comprising an application of a herbicidally-effective amount of a compound of claim 18 to the locus of said weeds.

77. A method for the control of weeds comprising an application of a herbicidally-effective amount of a compound of claim 19 to the locus of said weeds.

78. A method for the control of weeds comprising an application of a herbicidally-effective amount of a compound of claim 20 to the locus of said weeds.

79. A method for the control of weeds comprising an application of a herbicidally-effective amount of a compound of claim 21 to the locus of said weeds.

80. A method for the control of weeds comprising an application of a herbicidally-effective amount of a compound of claim 22 to the locus of said weeds.

81. A method for the control of weeds comprising an application of a herbicidally-effective amount of a compound of claim 23 to the locus of said weeds.

82. A method for the control of weeds comprising an application of a herbicidally-effective amount of a compound of claim 24 to the locus of said weeds.

83. A method for the control of weeds comprising an application of a herbicidally-effective amount of a compound of claim 25 to the locus of said weeds.

84. A method for the control of weeds comprising an application of a herbicidally-effective amount of a compound of claim 26 to the locus of said weeds.

85. A method for the control of weeds comprising an application of a herbicidally-effective amount of a compound of claim 27 to the locus of said weeds.

86. A method for the control of weeds comprising an application of a herbicidally-effective amount of a compound of claim 28 to the locus of said weeds.

87. A method for the control of weeds comprising an application of a herbicidally-effective amount of a compound of claim 29 to the locus of said weeds.

* * * * *